United States Patent
Uitbeijerse et al.

(10) Patent No.: US 9,393,440 B2
(45) Date of Patent: Jul. 19, 2016

(54) HEAT RECOVERING SYSTEM FOR LIGHT THERAPY DEVICE

(71) Applicant: KONINKLIJKE PHILIPS N.V., Eindhoven (NL)

(72) Inventors: Bastiann Uitbeijerse, Helmond (NL); Georges Marie Calon, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/241,453

(22) PCT Filed: Sep. 24, 2012

(86) PCT No.: PCT/IB2012/055067
§ 371 (c)(1),
(2) Date: Feb. 27, 2014

(87) PCT Pub. No.: WO2013/046113
PCT Pub. Date: Apr. 4, 2013

(65) Prior Publication Data
US 2014/0228917 A1 Aug. 14, 2014

Related U.S. Application Data

(60) Provisional application No. 61/538,976, filed on Sep. 26, 2011.

(51) Int. Cl.
*A61N 5/06* (2006.01)

(52) U.S. Cl.
CPC ............ *A61N 5/0625* (2013.01); *A61N 5/0616* (2013.01); *A61N 2005/0645* (2013.01); *A61N 2005/0652* (2013.01); *A61N 2005/0653* (2013.01); *A61N 2005/0654* (2013.01)

(58) Field of Classification Search
CPC ........... A61N 5/062; A61N 2005/0651; A61N 2005/0652; A61N 2005/00654; A61N 2005/0642; A61N 2005/0643; A61N 2005/0644; A61N 2005/0659; A61F 7/007; A61F 2007/0075
USPC .......... 607/88–91, 96, 98–102; 606/9, 10, 13, 606/27–31; 128/898
See application file for complete search history.

(56) References Cited

U.S. PATENT DOCUMENTS

| | | | | |
|---|---|---|---|---|
| 5,301,090 | A | * | 4/1994 | Hed ............................... 362/558 |
| 5,957,960 | A | * | 9/1999 | Chen et al. ...................... 607/92 |
| 6,096,066 | A | * | 8/2000 | Chen et al. ...................... 607/88 |

(Continued)

FOREIGN PATENT DOCUMENTS

| | | |
|---|---|---|
| EP | 0674468 A2 | 9/1995 |
| WO | 2006063318 A1 | 6/2006 |
| WO | 2012023086 A1 | 2/2012 |

*Primary Examiner* — Ahmed Farah

(57) ABSTRACT

The invention relates to a radiation emitting device (1) for application near mammal tissue (2), comprising: a substrate (3) having a front surface (4) and an opposing back surface (5), said substrate accommodating at least one radiation source (6) on said front surface (4). Said at least one radiation source (6) is arranged for applying energy on said mammal tissue (2). A heat spreading section (7) is arranged on said back surface (5) of said substrate (3) in thermal contact with said at least one radiation source (6). Said heat spreading section (7) has an extended area (8) extending beyond said substrate (3) in a direction substantially parallel to said substrate (3). Said extended area (8) of said heat spreading section (7) is arranged in thermal contact with said mammal tissue (2).

13 Claims, 1 Drawing Sheet

(56) References Cited

U.S. PATENT DOCUMENTS

| | | | |
|---|---|---|---|
| 6,290,713 B1 | 9/2001 | Russell | |
| 6,887,260 B1 * | 5/2005 | McDaniel | 607/88 |
| 2003/0009205 A1 * | 1/2003 | Biel | 607/88 |
| 2005/0237739 A1 * | 10/2005 | Lee | A61N 5/0613 362/241 |
| 2009/0287195 A1 * | 11/2009 | Altshuler et al. | 606/9 |
| 2010/0211059 A1 * | 8/2010 | Deem | A61B 18/1815 606/33 |
| 2011/0098789 A1 | 4/2011 | Weckwerth et al. | |
| 2013/0144364 A1 * | 6/2013 | Wagenaar Cacciola et al. | 607/90 |

\* cited by examiner

US 9,393,440 B2

HEAT RECOVERING SYSTEM FOR LIGHT THERAPY DEVICE

CROSS-REFERENCE TO PRIOR APPLICATIONS

This application is the U.S. National Phase application under 35 U.S.C. §371 of International Application No. PCT/IB2012/055067, filed on Sep. 24, 2012, which claims the benefit of U.S. Provisional Patent Application No. 61/538,976, filed on Sep. 26, 2011. These applications are hereby incorporated by reference herein.

FIELD OF THE INVENTION

The present invention relates to radiation or light therapy devices for use near mammal tissue. More specifically, the present invention relates to light therapy devices comprising a heat recovering system for reuse of residual heat from the light source.

BACKGROUND OF THE INVENTION

It is known that radiation or lighting systems using LEDs and/or OLEDs will perform better at low temperatures. Therefore, each such lighting system will have a cooling system to limit the temperature of the LEDs and/or OLEDs.

When using radiation emitting devices for application near mammal tissue, it is very important to control and limit the temperature of the irradiated tissue. In general, thermal losses in terms of residual heat from LED and/or OLED devices will be removed via passive or active cooling, e.g., a heat sink with or without fan, to the environment. In case such a system is not desirable, then the electrical power input to the LEDs and/or OLEDs may instead be limited, such that the heat produced by the LEDs and/or OLEDs does not raise the tissue temperature above acceptable levels.

Solutions suggested in the prior art all intend to remove heat from the radiation emitting device to the ambient by using heat sinking, as, e.g., the flexible illuminator suggested in U.S. Pat. No. 6,290,713. However, this solution lacks efficiency when radiation emitting devices for application near mammal tissue are discretely worn under clothing, which will limit heat dissipation to the environment.

Safety is very important with respect to medical devices, specifically also for devices that are used in direct contact with mammal tissue, such as human skin. It must be guaranteed that in case of a device failure, no risks for the user/patient are induced.

SUMMARY OF THE INVENTION

It would be advantageous to have light emitting device for application near mammal tissue that effectively deals with heat generated by the device in a safe manner for the mammal tissue. It would further be desirable to achieve a light emitting device for application near mammal tissue that is safe for operating under clothing.

To better address one or more of these concerns, in a first aspect of the invention a radiation emitting device for application near mammal tissue is provided, comprising a substrate having a front surface and an opposing back surface, said substrate accommodating at least one radiation source on said front surface wherein said at least one radiation source is arranged for irradiating said mammal tissue in a radiation emitting area; a heat spreading section arranged on said back surface of said substrate in thermal contact with said at least one radiation source; wherein said heat spreading section has an extended area extending beyond said substrate in a direction substantially parallel to said substrate, and wherein said extended area of said heat spreading section is arranged in thermal contact with said mammal tissue when the radiation emitting device is applied near said mammal tissue. The heat spreading section may, e.g., be a flat heat spreading section, since a suitable shape of a radiation emitting device for application near mammal tissue often is flat.

The radiation source may be any energy source able to apply energy to said mammal tissue. In an embodiment of the invention, the radiation source is, however a light source additionally used for light therapy.

In the context of this application, the term "in thermal contact" refers to the ability to exchange heat energy between two systems, for example between the radiation source and the heat spreading section or between the extended area of the heat spreading section and the mammal tissue. Thermal contact does not necessarily require that the systems be in direct physical contact; there may for example be a thermally conducting material positioned in between the systems. Thermal contact established a preferred path for heat transfer between the two systems.

Thus, a radiation emitting device is presented having a radiation emitting area irradiating the mammal tissue, e.g. human skin, and a dark area at least partially surrounding the radiation emitting area, into which dark area the extended area of the heat spreading section extends. The heat spreading section transports heat losses and residual heat from the radiation emitting area to extended area, i.e. the dark area of the device close to the skin. The thermal contact of the heat spreading section's extended area with the skin in the dark area, preferably a substantial part thereof, effectively removes heat from the 'hot' area, i.e. the radiation emitting area where the heat is generated, and reuses the heat in the 'cold' area, i.e. the dark area of the radiation emitting device, into which the heat spreading section extends via the extended area. When the radiation source is a light source, the radiation emitting area may be referred to as the light emitting area and the phrase "the heat spreading section has an extended area extending beyond said substrate" may also be written "the heat spreading section has an extended area extending beyond the light emitting area into the dark area". In operation, with the radiation sources in the radiation emitting area producing both functional radiation and residual heat, the user will experience a more uniform heat distribution across a larger area of the radiation emitting device, thereby also increasing the therapeutic effect of heat on the skin. In a preferred embodiment the extended area of the heat spreading section has a size at least 25% of the size of the light emitting area. This guarantees a perceptible heat transfer to the mammal tissue in a peripheral area around the light emitting area. In more preferred embodiments, the size of the extended area of the heat spreading section is at least 50% or even at least 100% of the size of the light emitting area. An extended area of a size that large substantially contributes to additional heat transfer to the mammal tissue and substantially extends the operating area of the radiation emitting device beyond the light emitting area.

Because a significant amount of heat can be removed from the radiation or light emitting area, a higher radiation output in terms of intensity or lumen per area can be applied without substantially increasing the skin temperature outside a safe operating window. Higher radiation output results in a more effective therapeutic treatment, and the additional residual heat is effectively removed and reused to warm up the surrounding skin, which in addition provides a synergetic effect as a therapeutic healing radiation wavelength is more effective in combination with warmth stimulation. Reuse of residual heat in radiation therapy devices is especially advantageous in applications for pain relief, where warmth, next to a therapeutically healing wavelength, provides a soothing and relaxing effect on muscles.

The radiation emitting device may further comprise at least one additional electrical component arranged on said substrate, wherein said at least one additional electrical component also is in thermal contact with said heat spreading section. In that way, also the residue heat from the electronics may be reused. The discussed advantages of reuse of heat are thus also achieved in combination with the other electronic components in the radiation emitting device.

The heat spreading section and the extended area thereof may also make the device intrinsically safe, due to the fact that when a malfunction occurs (e.g., short-circuit in electronics or batteries) the heat dissipation will spread out over a large surface area, reducing the speed of temperature increase, and giving the user enough time to remove the device from the body. Since the heat is directed to the body, instead of to the backside of the device, the user will feel a malfunction quickly, before any fire hazard occurs with the clothes a user may wear over the device.

The additional electrical component may be a component chosen from the group consisting of: a battery, a microprocessor, and any other electrical equipment useful for a radiation emitting device.

The radiation emitting device may comprise an insulating layer arranged to cover the heat spreading section, so that heat losses to the ambient atmosphere are minimized. In that way, the energy losses from the radiation source and other electronics are reused to an as high extent as possible. It also makes it irrelevant for the functioning of the device if the person wearing it has clothes covering the radiation emitting device or not. This is an advantage in the user's everyday life, as the user does not have to worry about the device or its operation when dressing or undressing in different situations, e.g. when going outside when it is cold and warm clothes are required, or when going to or from the bed, which may be frequent for a person healing from injuries. The insulating layer may be made of textile or foam or any suitable insulating material that is flexible and comfortable to use.

The extended area of the heat spreading section may extend beyond the substrate in one particular direction or the extended area may extend beyond the substrate in all directions thereby completely surrounding the radiation or light emitting area.

The contact of said extended area with said mammal tissue may be arranged to prevent radiation, in at least one direction parallel to said substrate, from leaking out from the device. Radiation leakage from the device may further be prevented in all directions parallel to said substrate. Radiation leakage may be annoying to a user, and may also be hazardous for the user or other persons if the radiation or light therapy is performed in the UV and/or IR domains. The discrete use of the device is also facilitated.

The radiation source of the radiation emitting device may be a LED, an incandescent lamp, and/or a gas discharge lamp. The radiation source may be any radiation source suitable to use in a therapeutic device using radiation on mammal tissue. LEDs are preferred due to their low power usage, improving the battery time of the device and reducing the amount of residual heat that needs to be spread out and lead away from the radiation source. In one embodiment, LEDs are arranged in a two-dimensional array characterized by a regular distance between neighboring LEDs, referred to as the pitch of the array. The radiation or light emitting area may then be considered to be the continuous area covered by the array wherein this continuous area extends half of pitch distance past the peripheral LEDs.

In case of a high power radiation source or power consuming additional electronic components, the surface area of said extended area and a thermal contact area of said extended area with said mammal tissue may be increased as a function of the amount of additional heat produced from these components and spread by said heat spreading section. The area of the heat spreading section is thus chosen to provide a sufficient heat spreading effect for the electronics and radiation source used. If more power is used in the device, e.g. due to use of an incandescent radiation source, the area of the heat spreading section and thus the device may be made larger.

The extended area of the radiation emitting device may be made of a thermally conductive and flexible material. The heat spreading section and the device may then be wrapped around, e.g. an arm, following the contours of the body, increasing the comfort of wearing the device, while at the same time increasing the contact area to the mammal tissue used for spreading the heat from the radiation source and electronic components. The extended area may further be made of a light weight material to improve the user experience, reducing the awareness of the user for the (additional) weight of the device, and thus increase the comfort of wearing the device.

The radiation emitting device may be used on any mammal, e.g. a human. The same effects and most of the advantages are, however, also gained when the device is used for any mammal animal treated with radiation therapy.

In a further aspect of the invention a method of radiation mammal tissue is provided wherein the mammal tissue is irradiated with radiation from at least one radiation source and thermal energy from the at least one radiation source is spread to an extended area of a heat spreading section and thermally conducted from at least part of the extended area of the heat spreading section to the mammal tissue. In a preferred embodiment the radiation source is a light source emitting both light and heat to the mammal tissue.

The advantages attributed to features of the light emitting device described above vis-à-vis apply to the method described in this paragraph and include amongst others a increased heat spreading area, maximum reuse of residual heat and a larger action area (i.e. effectively treated mammal tissue area) of the radiation therapy.

It is noted that the invention relates to all possible combinations of features recited in the claims.

BRIEF DESCRIPTION OF THE DRAWINGS

The above objects, as well as additional objects, features and advantages of the present invention, will be more fully appreciated by reference to the following illustrative and non-limiting detailed description of preferred embodiments of the present invention, when taken in conjunction with the accompanying drawings, wherein.

As illustrated in the figures, the sizes of layers and regions are exaggerated for illustrative purposes and, thus, are provided to illustrate the general structures of embodiments of the present invention. Like reference numerals refer to like elements throughout.

DETAILED DESCRIPTION OF THE EMBODIMENTS

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and to fully convey the scope of the invention to the skilled person.

Figure 1:
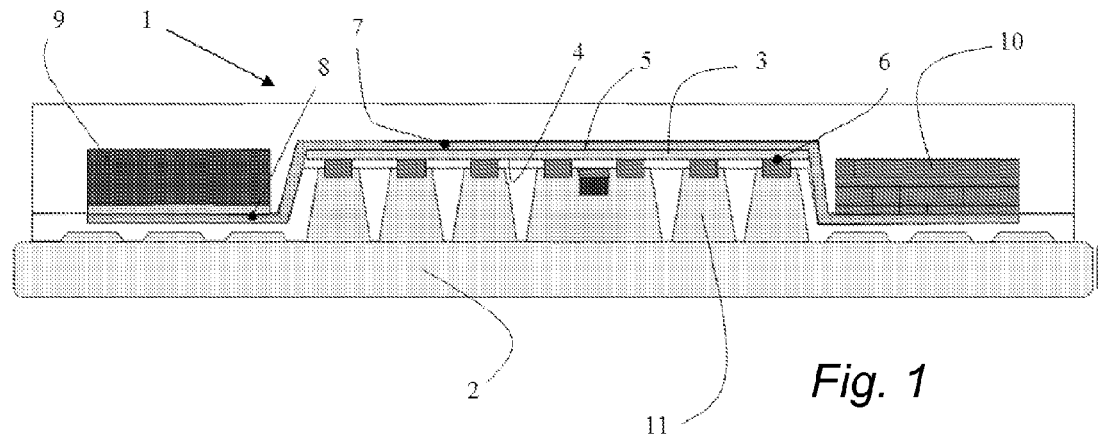
FIG. 1 shows a cross sectional view of a radiation emitting device according to an embodiment of the invention.

FIG. 1 is a schematic representation of a radiation emitting device 1 according to a first embodiment of the invention.

An array of radiation emitting diodes LEDs 6 is arranged on a flexible substrate, such as a flexible PCB (e.g., kapton foil) or an electronic textile. The radiation emitted by the LEDs 6 is directed towards the mammal tissue 2, for photonic therapy. The radiation emitting device is thus configured to operate as a direct lit system. A fixed distance between the LEDs 6 and the mammal tissue 2 is secured by means of a spacer 11 having holes, with air therein, for supporting the LEDs 6. In addition to preserving a distance between the LEDs 6 and the skin 2, the spacer has a soft touch on the mammal tissue 2. A three-dimensional flexible foam may be used to combine both of these functionalities.

Next to radiation in the form of light, the LEDs 6 also generate heat, of which a certain amount is emitted in the direction of the mammal tissue 2, along with the light. In operation, a user is therefore subjected to light and heat radiation across a first therapeutic area of mammal tissue 2 facing the LED array size. This area may be considered the radiation or light emitting area referred to above.

Figure 2:
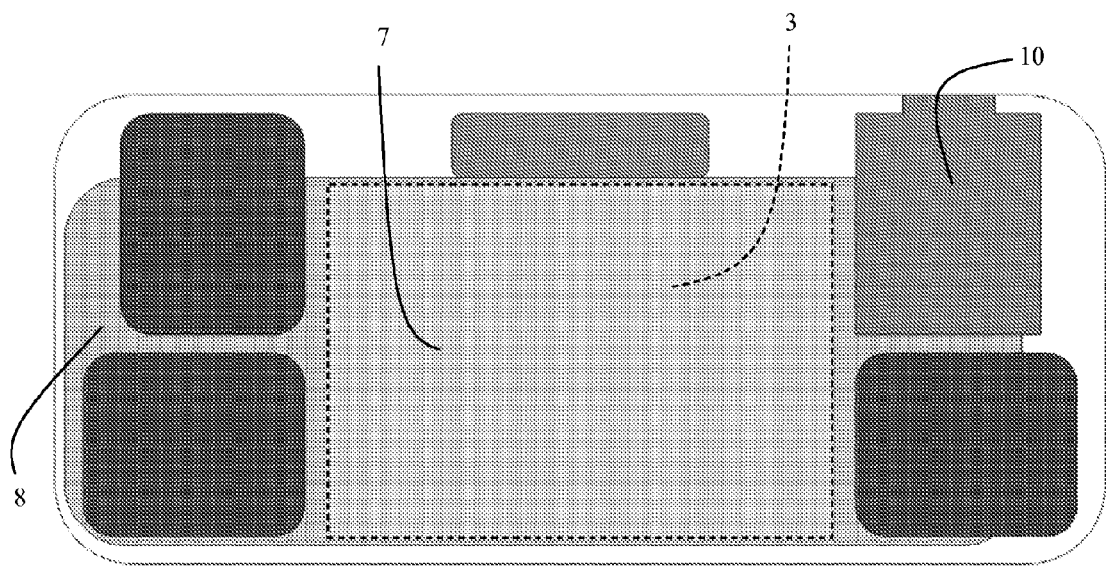
FIG. 2 shows a top view of the radiation emitting device according to an embodiment of the invention.

A heat spreading section 7 is positioned at the back side of the LED substrate and removes residual heat (i.e. heat not transferred via direct emission to the mammal tissue 2) from the LEDs 6. The heat spreading section as depicted in FIG. 1 and FIG. 2 is substantially larger than the size of the LED array and the extended area 8 is bent towards the mammal tissue 2 along at least a part of the periphery of the LED array (e.g. to the left side and right side of the array). The extended area 8 of the heat spreading section 7 is in thermal contact with the mammal tissue 2. Hence, heat removed from the LEDs 6 is conducted sideways via the heat spreading section and conducted or emitted towards the mammal tissue 2. In FIG. 1 a thin layer is arranged between the extended area 8 of the heat spreading section 7 and the mammal tissue 2, which layer may for example be of the same material and structure as the spacer mentioned above (e.g., a thin foam layer having a number of indentations or holes with a similar look and feel and similar surface structure as the LED spacer. The heat spreading section 7 thus extends the (main) radiation or light emitting area with a (additional) heat radiating area partially surrounding the (main) radiation or light emitting area. The heat spreading section 7 may be manufactured from any known thermally conducting substrate or foil material.

FIG. 1 and FIG. 2 also depict other components of the device, such as batteries 9, a PCB 10 with a controller and electronics for driving the LEDs 6, and an overall cover or envelope which may be based on a textile and foam materials.

The embodiment shown in FIG. 1 may for example be a flexible radiation emitting device suitable for pain relief, where warmth may provide for a substantial part of the therapeutic effect.

By using a thin thermally conductive substrate 5, the heat spreading section can be designed such that the therapeutic area is substantially enlarged while still providing a device that is flexible and light weight and therefore comfortable to wear.

In addition to the advantage that residual heat is effectively reused, a device 1 according an embodiment of the invention will also have minimal losses to the ambient atmosphere, which is especially beneficial when used as a therapy device that is to be worn underneath clothing etc.

An additional advantage of the invention is that the heat spreading section 7 may also operate as a protective layer inside the device to spread accidental heat seeds in a small area (e.g. due to short circuits) across a larger area, thereby preventing skin burns.

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein a plurality of heat sources (resistors, incandescent lamps, diodes, etc.) are used, in addition to the radiation source or replacing the radiation sources. Such a device may advantageously be used for pain relief, where the soothing effect of heat provides relaxation to the mammal tissue 2.

The skilled person also understands that to in order to apply heat energy to the mammal tissue, it is also possible to use direct thermal contacting equipment or electrodes positioned onto or even intruding the mammal tissue. The inventive concept of the present invention also applies to using any other means for heating the mammal tissue instead of the radiation source.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A radiation emitting device for application near mammal tissue, comprising:
    a substrate having a front surface and an opposing back surface, said substrate accommodating at least one radiation source on said front surface wherein said at least one radiation source is arranged for applying radiation to said mammal tissue;
    a heat spreading section arranged on said back surface of said substrate in thermal contact with said at least one radiation source;
    wherein said heat spreading section has an extended area extending beyond said substrate in a direction substantially parallel to said substrate and wherein at least part of said extended area of said heat spreading section is arranged to be in thermal contact with said mammal tissue when said radiation emitting device is applied near said mammal tissue; and,
    wherein said extended area has a surface area, and said substrate has a surface area; wherein the surface area of said extended area is at least 25% of the surface area of said substrate.

2. The radiation emitting device according to claim 1, further comprising at least one electrical component, wherein said at least one electrical component is in thermal contact with said heat spreading section and wherein the electrical component is a component chosen from the group consisting of a battery, a microprocessor or an electronic component for driving at least one radiation source.

3. The radiation emitting device according to claim 2, wherein a surface area of said extended area and a thermal contact area of said extended area with said mammal tissue is further dimensioned based on an amount of heat generated by said at least one electronic component.

4. The radiation emitting device according to claim 1, further comprising an insulating layer arranged to cover said heat spreading section.

5. The radiation emitting device according to claim 1, wherein said extended area is arranged in at least one direction parallel to said substrate.

6. The radiation emitting device according to claim 1, wherein said extended area is arranged in all directions parallel to said substrate.

7. The radiation emitting device according to claim 1, wherein said at least one radiation source is at least one chosen from the group consisting of: a LED, an incandescent lamp, a gas discharge lamp, and a heat emitting elements.

8. The radiation emitting device according to claim 1, where said extended area is further arranged to prevent radiation from leaking out from the device.

9. The radiation emitting device according to claim 1, wherein said extended area is made of a thermally conductive and flexible material.

10. The radiation emitting device according to claim 1, wherein said mammal is a human.

11. Use of a radiation emitting device according to claim 1, for pain relief.

12. A method of radiation mammal tissue, comprising the steps of:
providing a substrate having a front surface and an opposing back surface, said substrate accommodating at least one radiation source on said front surface;
providing a heat spreading section arranged on said back surface of said substrate in thermal contact with said at least one radiation source, wherein said heat spreading section has an extended area extending beyond said substrate in a direction substantially parallel to said substrate;
radiating an area of said mammal tissue with radiation from said at least one radiation source;
spreading thermal energy from said at least one radiation source to said extended area of said heat spreading section, and;
conducting thermal energy from at least part of said extended area of said heat spreading section to a region of said mammal tissue located outside of the radiated area; and,
wherein said extended area has a surface area, and said substrate has a surface area; wherein the surface area of said extended area is at least 25% of the surface area of said substrate.

13. The method according to claim 12, wherein said at least one radiation source is a light source and wherein radiating said mammal tissue with radiation from said at least one radiation source comprises emitting light and radiating heat from said at least one light source to said mammal tissue.

* * * * *